US005496699A

United States Patent [19]
Sorenson

[11] Patent Number: 5,496,699
[45] Date of Patent: Mar. 5, 1996

[54] DETECTION OF ALLELE - SPECIFIC MUTAGENS

[75] Inventor: George D. Sorenson, Meriden, N.H.

[73] Assignee: Trustees of Darmouth College, Hanover, N.H.

[21] Appl. No.: 142,845

[22] Filed: Oct. 25, 1993

Related U.S. Application Data

[63] Continuation of Ser. No. 874,845, Apr. 27, 1992.
[51] Int. Cl.$^6$ ..................................................... C12Q 1/68
[52] U.S. Cl. ........................... 435/6; 435/91.2; 536/24.33
[58] Field of Search .................................. 435/91.2, 5, 6; 536/24.33; 935/78

[56] References Cited

U.S. PATENT DOCUMENTS

| 4,988,617 | 1/1991 | Landegren et al. | 435/6 |
| 5,068,175 | 11/1991 | Prashad | 435/6 |
| 5,137,806 | 8/1992 | LeMaistre et al. | 435/5 |

FOREIGN PATENT DOCUMENTS

| 8702064 | 4/1987 | WIPO . |
| 8900206 | 1/1989 | WIPO . |

OTHER PUBLICATIONS

Sidransky, D. et al., Science, 256:102–105 (1992).
Baranv, F., PNAS, 87:8923–8927 (1991).
Landgraf, A. et al., Analytical Biochem., 193:231–235 (1991).
Murakami et al., Ca. Res., 51:3356–3362 (1991).
Stork et al., Oncogene. 6:857–862 (1991).
Saiki, R. K., Amplification of Genomic DNA in PCR Protocols, (Acad. Press Inc.), San Diego, p. 13 (1990).
Nickerson et al., PNAS, 87:8923–8927 (1990).
Gilliland et al., PNAS, 87:2725–2729 (1990).
Gilliland et al., "Competitive PCR for Quantitation of MRNA", PCR Protocols, (Acad. Press) pp. 60–69 (1990).
Vallette et al, Nucleic Acids Res., 17:723–33 (1989).
Higuchi et al., Nucleic Acids Res., 16:7351–67 (1988).
Fournie, G. J. et al., Analytical Biochem., 158:250–56 (1986).
Verlaan–de Vries et al., Gene, 50:313–320 (1986).
Steinman, C. R., J. Clin. Invest., 73:832–841 (1984).
Shapiro et al., Cancer, 51:2116–2120 (1983).
Dennin, R. H., Klin, Wochenschr., 57:451–456 (1979).
Leon, S. A. et al., "Free DNA In The Serum Of Cancer Patients and The Effect of Therapy", *Cancer Research* 37:646–650 (Mar. 1977).
Barany, F., "The Ligase Chain Reaction In A PCR World", *PCR Methods and Applications*, 1:5–16 (1991).
Weiss, R., "Hot Prospect For New Gene Amplifier", *Science* 254:1292–1293 (Nov. 29, 1991).
1988 Stratagene Catalog, p. 39.
Translation (English) of WO89/00206.
Martin et al., Human Immunology, (Feb. 1992) 33:108–113.

*Primary Examiner*—W. Gary Jones
*Assistant Examiner*—Scott W. Houtteman
*Attorney, Agent, or Firm*—Lahive & Cockfield

[57] ABSTRACT

Methods are provided for detecting and quantitating gene sequences, such as mutated genes and oncogenes, in biological fluids. The fluid sample (e.g., plasma, serum, urine, etc.) is obtained, deproteinized and the DNA present in the sample is extracted. Following denaturation of the DNA, an amplification procedure, such as PCR or LCR, is conducted to amplify the mutated gene sequence.

21 Claims, 3 Drawing Sheets

DETECTION OF ALLELE - SPECIFIC MUTAGENS

GOVERNMENT SUPPORT

The research leading to this invention was supported by government funding pursuant to NIH Grant No. CA 47248.

This application is a continuation of application Ser. No. 07/874,845, filed on Apr. 27, 1992.

BACKGROUND OF THE INVENTION

Soluble DNA is known to exist in the blood of healthy individuals at concentrations of about 5 to 10 ng/ml. It is believed that soluble DNA is present in increased levels in the blood of individuals having autoimmune diseases, particularly systemic lupus erythematosus (SLE) and other diseases including viral hepatitis, cancer and pulmonary embolism. It is not known whether circulating soluble DNA represents a specific type of DNA which is particularly prone to appear in the blood. However, studies indicate that the DNA behaves as double-stranded DNA or as a mixture of double-stranded and single-stranded DNA, and that it is likely to be composed of native DNA with single-stranded regions. Dennin, R. H., *Klin. Wochenschr.* 57:451–456, (1979). Steinman, C. R., *J. Clin. Invest.*, 73:832–841, (1984). Fournie, G. J. et al., *Analytical Biochem.* 158:250–256, (1986). There is also evidence that in patients with SLE, the circulating DNA is enriched for human repetitive sequence (Alu) containing fragments when compared to normal human genomic DNA.

In patients with cancer, the levels of circulating soluble DNA in blood are significantly increased. Types of cancers which appear to have a high incidence of elevated DNA levels include pancreatic carcinoma, breast carcinoma, colorectal carcinoma and pulmonary carcinoma. In these forms of cancer, the levels of circulating soluble DNA in blood are usually over 50 ng/ml, and generally the mean values are more than 150 ng/ml. Leon et al., *Can. Res.* 37:646–650, 1977; Shapiro et al., *Cancer* 51:2116–2120, 1983.

Mutated oncogenes have been described in experimental and human tumors. In some instances certain mutated oncogenes are associated with particular types of tumors. Examples of these are adenocarcinomas of the pancreas, colon and lung which have approximately a 75%, 50%, and 35% incidence respectively, of Kirsten ras (K-ras) genes with mutations in positions 1 or 2 of codons 12. The most frequent mutations are changes from glycine to valine (GGT to GTT), glycine to cysteine (GGT to TGT), and glycine to aspartic acid (GGT to GAT). Other, but less common mutations of codon 12 include mutations to AGT and CGT. K-ras genes in somatic cells of such patients are not mutated.

The ability to detect sequences of mutated oncogenes or other genes in small samples of biological fluid, such as blood plasma, would provide a useful diagnostic tool. The presence of mutated K-ras gene sequences in the plasma would be indicative of the presence in the patient of a tumor which contains mutated oncogenes. Presumably this would be a specific tumor marker since there is no other known source of mutated K-ras genes. Therefore, this evaluation may be useful in suggesting and/or confirming a diagnosis. The amount of mutated K-ras sequences in the plasma may relate to the size of the tumor, the growth rate of the tumor and/or the regression of the tumor. Therefore, serial quantitation of mutated K-ras sequences may be useful in determining changes in tumor mass. Since most human cancers have mutated oncogenes, evaluation of plasma DNA for mutated sequences may have very wide applicability and usefulness.

SUMMARY OF THE INVENTION

This invention recognizes that gene sequences (e.g., oncogene sequences) exist in blood, and provides a method for detecting and quantitating gene sequences such as from mutated oncogenes and other genes in biological fluids, such as blood plasma and serum. The method can be used as a diagnostic technique to detect certain cancers and other diseases which tend to increase levels of circulating soluble DNA in blood. Moreover, this method is useful in assessing the progress of treatment regimes for patients with certain cancers.

The method of the invention involves the initial steps of obtaining a sample of biological fluid (e.g., urine, blood plasma or serum, sputum, cerebral spinal fluid), then deproteinizing and extracting the DNA. The DNA is then amplified by techniques such as the polymerase chain reaction (PCR) or the ligase chain reaction (LCR) in an allele-specific manner to distinguish a normal gene sequence from a mutated gene sequence present in the sample. In one embodiment where the location of the mutation is known, the allele specific PCR amplification is performed using four pairs of oligonucleotide primers. The four primer pairs include a set of four allele-specific first primers complementary to the gene sequence contiguous with the site of the mutation on the first strand. These four primers are unique with respect to each other and differ only at the 3' nucleotide which is complementary to the wild type nucleotide or to one of the three possible mutations which can occur at this known position. The four primer pairs also include a single common primer which is used in combination with each of the four unique first strand primers. The common primer is complementary to a segment of a second strand of the DNA, at some distance from the position of the first primer.

This amplification procedure amplifies a known base pair fragment which includes the mutation. Accordingly, this technique has the advantage of displaying a high level of sensitivity since it is able to detect only a few mutated DNA sequences in a background of a $10^7$-fold excess of normal DNA. The method is believed to be of much greater sensitivity than methods which detect point mutations by hybridization of a PCR product with allele-specific radiolabelled probes which will not detect a mutation if the normal DNA is in more than 20-fold excess.

The above embodiment is useful where a mutation exists at a known location on the DNA. In another embodiment where the mutation is known to exist in one of two possible positions, eight pair of oligonucleotide primers may be used. The first set of four primer pairs (i.e., the four unique, allele-specific primers, each of which forms a pair with a common primer) is as described above. The second set of four primer pairs comprises four allele-specific primers complementary to the gene sequence contiguous with the site of the second possible mutation on the sense strand. These four primers are unique with respect to each other and differ at the terminal 3' nucleotide which is complementary to the wild type nucleotide or to one of the three possible mutations which can occur at this second known position. Each of these allele-specific primers is paired with another common primer complementary to the other strand, distant from the location of the mutation.

The PCR techniques described above preferably utilize a DNA polymerase which lacks 3'exonuclease activity and therefore the ability to proofread. A preferred DNA polymerase is *Thermus aquaticus* DNA polymerase.

During the amplification procedure, it is usually sufficient to conduct approximately 30 cycles of amplification in a DNA thermal cycler. After an initial denaturation period of 5 minutes, each amplification cycle preferably includes a denaturation period of about 1 minute at 95° C., primer annealing for about 2 minutes at 58° C. and an extension at 72° C. for approximately 1 minute.

Following the amplification, aliquots of amplified DNA from the PCR can be analyzed by techniques such as electrophoresis through agarose gel using ethidium bromide staining. Improved sensitivity may be attained by using labelled primers and subsequently identifying the amplified product by detecting radioactivity or chemiluminescense on film. Labelled primers may also permit quantitation of the amplified product which may be used to determine the amount of target sequence in the original specimen.

As used herein, allele-specific amplification describes a feature of the method of the invention where primers are used which are specific to a mutant allele, thus enabling amplification of the sequence to occur where there is 100% complementarity between the 3' end of the primer and the target gene sequence. Thus, allele-specific amplification is advantageous in that it does not permit amplification unless there is a mutated allele. This provides an extremely sensitive detection technique.

DETAILED DESCRIPTION OF THE INVENTION

Figure 1A:
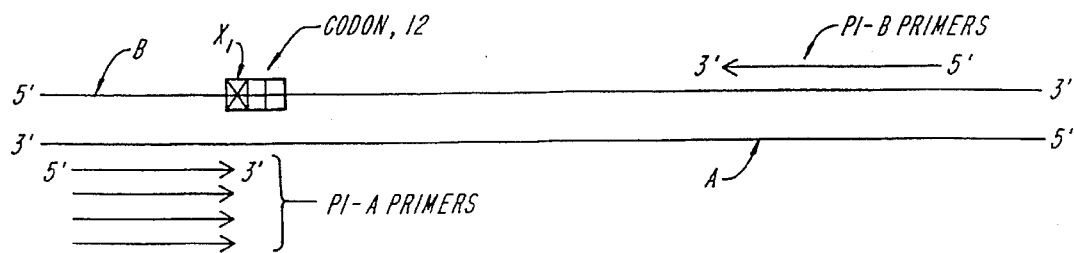
FIGS. 1A and 1B are diagramatic representations of the amplification strategy for the detection of a mutated K-ras gene with a mutation present at a single known location of K-ras.

The detection of mutated DNA, such as specific single copy genes, is potentially useful for diagnostic purposes, and/or for evaluating the extent of a disease. Normal plasma is believed to contain about 10 ng of soluble DNA per ml. The concentration of soluble DNA in blood plasma is known to increase markedly in individuals with cancer and some other diseases. The ability to detect the presence of known mutated gene sequences, such as K-ras gene sequences, which are indicative of a medical condition, is thus highly desirable.

The present invention provides a highly sensitive diagnostic method enabling the detection of such mutant alleles in biological fluid, even against a background of as much as a $10^7$-fold excess of normal DNA. The method generally involves the steps of obtaining a sample of a biological fluid containing soluble DNA, deproteinizing, extracting and denaturing the DNA, followed by amplifying the DNA in an allele-specific manner, using a set of primers among which is a primer specific for the mutated allele. Through this allele-specific amplification technique, only the mutant allele is amplified. Following amplification, various techniques may be employed to detect the presence of amplified DNA and to quantify the amplified DNA. The presence of the amplified DNA represents the presence of the mutated gene, and the amount of the amplified gene present can provide an indication of the extent of a disease.

This technique is applicable to the identification in biological fluid of sequences from single copy genes, mutated at a known position on the gene. Samples of biological fluid having soluble DNA (e.g., blood plasma, serum, urine, sputum, cerebral spinal fluid) are collected and treated to deproteinize and extract the DNA. Thereafter, the DNA is denatured. The DNA is then amplified in an allele-specific manner so as to amplify the gene bearing a mutation.

During deproteinization of DNA from the fluid sample, the rapid removal of protein and the virtual simultaneous deactivation of any DNase is believed to be important. DNA is deproteinized by adding to aliquots of the sample an equal volume of 20% NaCl and then boiling the mixture for about 3 to 4 minutes. Subsequently, standard techniques can be used to complete the extraction and isolation of the DNA. A preferred extraction process involves concentrating the amount of DNA in the fluid sample by techniques such as centrifugation.

The use of the 20% NaCl solution, followed by boiling, is believed to rapidly remove protein and simultaneously inactivate any DNases present. DNA present in the plasma is believed to be in the form of nucleosomes and is thus believed to be protected from the DNases while in blood. However, once the DNA is extracted, it is susceptible to the DNases. Thus, it is important to inactivate the DNases at the same time as deproteinization to prevent the DNases from inhibiting the amplification process by reducing the amount of DNA available for amplification. Although the 20% NaCl solution is currently preferred, it is understood that other concentrations of NaCl, and other salts, may also be used.

Other techniques may also be used to extract the DNA while preventing the DNases from affecting the available DNA. Because plasma DNA is believed to be in the form of nucleosomes (mainly histones and DNA), plasma DNA could also be isolated using an antibody to histones or other nucleosomal proteins. Another approach could be to pass the plasma (or serum) over a solid support with attached anti-histone antibodies which would bind with the nucleosomes. After rinsing the nucleosomes can be eluted from the antibodies as an enriched or purified fraction. Subsequently, DNA can be extracted using the above or other conventional methods.

In one embodiment, the allele-specific amplification is performed through the Polymerase Chain Reaction (PCR) using primers having 3' terminal nucleotides complementary to specific point mutations of a gene for which detection is sought. PCR preferably is conducted by the method described by Saiki, "Amplification of Genomic DNA", *PCR Protocols*, Eds. M. A. Innis, et al., Academic Press, San Diego (1990), pp. 13. In addition, the PCR is conducted using a thermostable DNA polymerase which lacks 3' exonuclease activity and therefore the ability to repair single base mismatches at the 3' terminal nucleotide of the DNA primer during amplification. As noted, a preferred DNA polymerase is *T. aquaticus* DNA polymerase. A suitable *T. aquaticus* DNA polymerase is commercially available from Perkin-Elmer as AmpliTaq DNA polymerase. Other useful DNA polymerases which lack 3' exonuclease activity include a Vent$_R$ (exo-), available from New England Biolabs, Inc., (purified from strains of *E. coli* that carry a DNA polymerase gene from the archaebacterium *Thermococcus litoralis*), Hot Tub DNA polymerase derived from *Thermus flauus* and available from Amersham Corporation, and Tth DNA polymerase derived form *Thermus thermo-*

*philus,* available from Epicentre Technologies, Molecular Biology Resource Inc., or Perkin-Elmer Corp.

This method conducts the amplification using four pairs of oligoucleotide primers. A first set of four primers comprises four allele-specific primers which are unique with respect to each other. The four allele-specific primers are each paired with a common distant primer which anneals to the other DNA strand distant from the allele-specific primer. One of the allele-specific primers is complementary to the wild type allele (i.e., is allele-specific to the normal allele) while the others have a mismatch at the 3' terminal nucleotide of the primer. As noted, the four unique primers are individually paired for amplification (e.g., by PCR amplification) with a common distant primer. When the mutated allele is present, the primer pair including the allele-specific primer will amplify efficiently and yield a detectable product. While the mismatched primers may anneal, the strand will not be extended during amplification.

The above primer combination is useful where a mutation is known to exist at a single position on an allele of interest. Where the mutation may exist at one of two locations, eight pair of oligonucleotide primers may be used. The first set of four pair is as described above. The second four pair or primers comprises four allele-specific oligonucleotide primers complementary to the gene sequence contiguous with the site of the second possible mutation on the sense strand. These four primers differ at the terminal 3' nucleotide which is complementary to the wild type nucleotide or to one of the three possible mutations which can occur at this second known position. Each of the four allele specific primers is paired with a single common distant primer which is complementary to the antisense strand upstream of the mutation.

During a PCR amplification using the above primers, only the primer which is fully complementary to the allele which is present will anneal and extend. The primers having a non-complementary nucleotide may partially anneal, but will not extend during the amplification process. Amplification generally is allowed to proceed for a suitable number of cycles, i.e., from about 20 to 40, and most preferably for about 30. This technique amplifies a mutation-containing fragment of the target gene with sufficient sensitivity to enable detection of the mutated target gene against a significant background of normal DNA.

The K-ras gene has point mutations which usually occur at one or two known positions in a known codon. Other oncogenes may have mutations at known but variable locations. Mutations with the K-ras gene are typically known to be associated with certain cancers such as adenocarcinomas of the lung, pancreas, and colon. FIGS. 1A through 2B illustrate a strategy for detecting, through PCR amplification, a mutation occurring at position 1 or 2 of the 12th codon of the K-ras oncogene. As previously noted, mutations at the first or second position of the 12th codon of K-ras are often associated with certain cancers such as adenocarcinomas of the lung, pancreas, and colon.

Figure 1B:
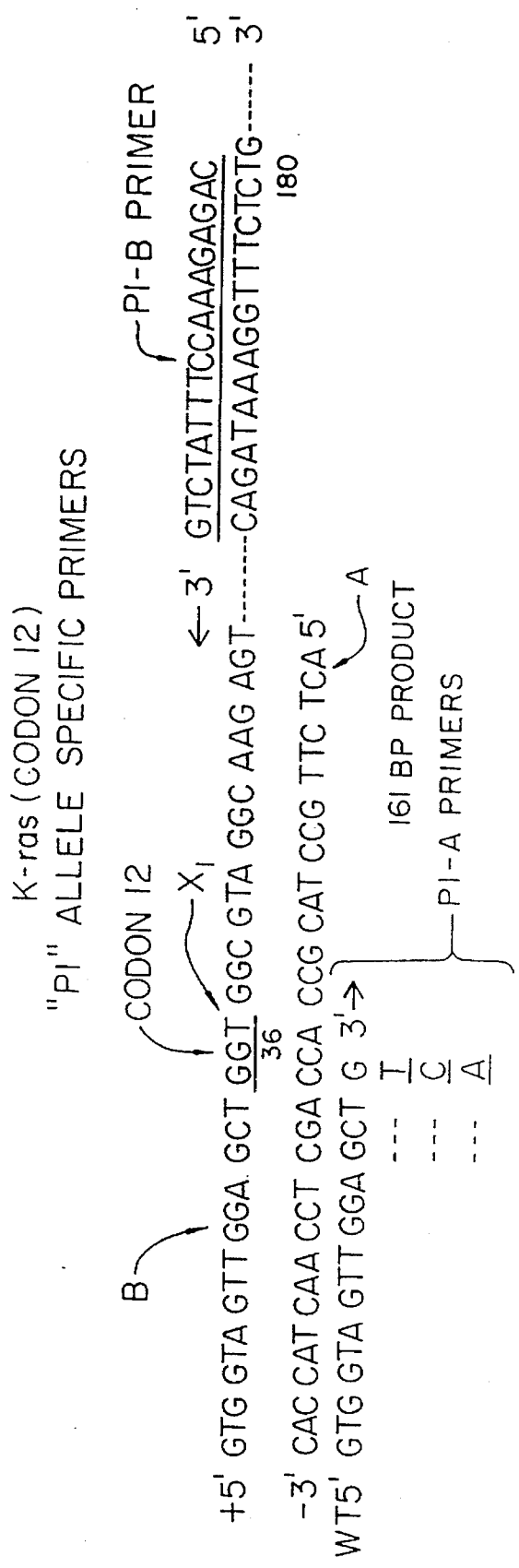

Referring to FIGS. 1A and 1B, the DNA from the patient sample is separated into two strands (A and B), which represent the sense and antisense strands. The DNA represents an oncogene having a point mutation which occurs on the same codon (i.e., codon 12) at position 1 ($X_1$). The allele-specific primers used to detect the mutation at position 1, include a set of four P1 sense primers (P1-A), each of which is unique with respect to the others. The four P1-A primers are complementary to a gene sequence contiguous with the site of the mutation on strand A. The four P1-A primers preferably differ from each other only at the terminal 3'nucleotide which is complementary to the wild type nucleotide or to one of the three possible mutations which can occur at this known position. Only the P1-A primer which is fully complementary to the mutation-containing segment on the allele will anneal and extend during amplification.

A common downstream primer (P1-B), complementary to a segment of the B strand downstream with respect to the position of the P1-A primers, is used in combination with each of the P1-A primers. The P1-B primer illustrated in FIG. 1 anneals to the allele and is extended during the PCR. Together, the P1-A and P1-B primers identified in Table 1 and illustrated in FIG. 1B amplify a fragment of the oncogene having 161 base pairs.

Figure 2A:
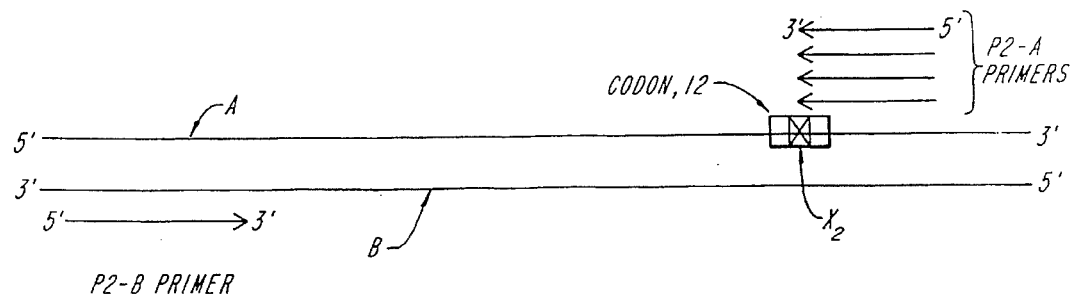
FIGS. 2A and 2B are diagramatic representations of the amplification strategy for detection of a mutated K-ras gene with a mutation present at a second of two possible locations of K-ras.
Figure 2B:
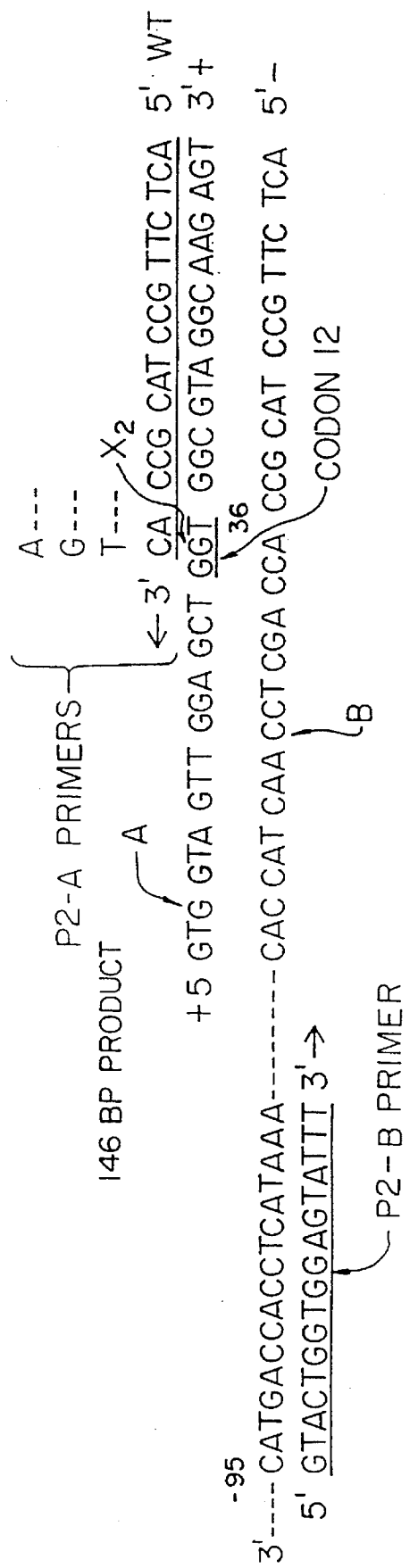

FIGS. 2A and 2B illustrate a scheme utilizing an additional set of four unique, allele-specific primers (P2-A) to detect a mutation which can occur at codon 12 of the oncogene, at position 2 ($X_2$). The amplification strategy illustrated in FIGS. 1A and 1B would be used in combination with that illustrated in FIGS. 2A and 2B to detect mutations at either position 1 ($X_1$) or position 2 ($X_2$) in Codon 12.

Referring to FIGS. 2A and 2B, a set of four unique allele-specific primers (P2-A) are used to detect a mutation present at a position 2 ($X_2$) of codon 12. The four P2-A primers are complementary to the genetic sequence contiguous with the site of the second possible mutation. These four primers are unique with respect to each other and preferably differ only at the terminal 3' nucleotide which is complementary to the wild type nucleotide or to one of the three possible mutations which can occur at the second known position ($X_2$).

A single common upstream primer (P2-B) complementary to a segment of the A strand upstream of the mutation, is used in combination with each of the unique P2-A primers. The P2-A and P2-B primers identified in Table 1 and illustrated in FIG. 2B will amplify a fragment having 146 base pairs.

During the amplification procedure, the polymerase chain reaction is allowed to proceed for about 20 to 40 cycles and most preferably for 30 cycles. Following an initial denaturation period of about 5 minutes, each cycle, using the AmpliTaq DNA polymerase, typically includes about one minute of denaturation at 95° C., two minutes of primer annealing at about 58° C., and a one minute extension at 72° C. While the temperatures and cycle times noted above are currently preferred, it is noted that various modifications may be made. Indeed, the use of different DNA polymerases and/or different primers may necessitate changes in the amplification conditions. One skilled in the art will readily be able to optimize the amplification conditions.

Exemplary DNA primers which are useful in practicing the method of this invention to detect the K-ras gene, having point mutations at either the first or second position in codon 12 of the gene, are illustrated in Table 1.

TABLE 1

Primers Used to Amplify (by PCR) Position 1 and 2 Mutations at Codon 12 of K-ras Gene
(5'–3')

| Sequence* | Strand | P1 or P2 |
| --- | --- | --- |
| GTGGTAGTTGGAGCTG | A | P1 |
| GTGGTAGTTGGAGCTC | A | P1 |
| GTGGTAGTTGGAGCTT | A | P1 |

TABLE 1-continued

Primers Used to Amplify (by PCR) Position 1
and 2 Mutations at Codon 12 of K-ras Gene
(5'–3')

| Sequence* | Strand | P1 or P2 |
|---|---|---|
| GTGGTAGTTGGAGCTA | A | P1 |
| CAGAGAAACCTTTATCTG | B | P1 |
| ACTCTTGCCTACGCCAC | A | P2 |
| ACTCTTGCCTACGCCAG | A | P2 |
| ACTCTTGCCTACGCCAT | A | P2 |
| ACTCTTGCCTACGCCAA | A | P2 |
| GTACTGGTGGAGTATTT | B | P2 |

*Underlined bases denote mutations.

The primers illustrated in Table 1 are, of course, merely exemplary. Various modifications can be made to these primers as is understood by those having ordinary skill in the art. For example, the primers could be lengthened or shortened, however the 3' terminal nucleotides must remain the same. In addition, some mismatches 3 to 6 nucleotides back from the 3' end may be made and would not be likely to interfere with efficacy. The common primers can also be constructed differently so as to be complementary to a different site, yielding either a longer or shorter amplified product.

In one embodiment, the length of each allele-specific primer can be different, making it possible to combine multiple allele-specific primers with their common distant primer in the same PCR reaction. The length of the amplified product would be indicative of which allele-specific primer was being utilized with the amplification. The length of the amplified product would indicate which mutation was present in the specimen.

The primers illustrated in Table 1 and FIGS. 1B and 2B, and others which could be used, can be readily synthesized by one having ordinary skill in the art. For example, the preparation of similar primers has been described by Stork et al., *Oncogene*, 6:857–862, 1991.

Other amplification methods and strategies may also be utilized to detect gene sequences in biological fluids according to the method of the invention. For example, another approach would be to combine PCR and the ligase chain reaction (LCR). Since PCR amplifies faster than LCR and requires fewer copies of target DNA to initiate, one could use PCR as first step and then proceed to LCR. Primers such as the common primers used in the allele-specific amplification described previously which span a sequence of approximately 285 base pairs in length, more or less centered on codon 12 of K-ras, could be used to amplify this fragment, using standard PCR conditions. The amplified product (approximately a 285 base pair sequence) could then be used in a LCR or ligase detection reaction (LDR) in an allele-specific manner which would indicate if a mutation was present. Another, perhaps less sensitive, approach would be to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F., PNAS 88: 189–193, 1991; Barany F., PCR Methods and Applications 1: 5–16, 1991). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the olignoucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

A variation of the reaction is the ligase detection reaction (LDR) which utilizes two adjacent oligonucleotides which are complementary to the target DNA and are similarly joined by DNA ligase (Barany F., PNAS 88:189–193, 1991). After multiple thermal cycles the product is amplified in a linear fashion. Thus the amount of the product of LDR reflects the amount of target DNA. Appropriate labeling of the primers allows detection of the amplified product in an allele-specific manner, as well as quantitation of the amount of original target DNA. One advantage of this type of reaction is that it allows quantitation through automation (Nickerson et al., PNAS 87: 8923–8927, 1990).

Examples of suitable oligonucleotides for use with LCR for allele-specific ligation and amplification to identify mutations at position 1 in codon 12 of the K-ras gene are illustrated below in Table 2.

TABLE 2

Oligonucleotides (5'–3') for use in LCR

| Sequence* | Strand | P1 or P2 |
|---|---|---|
| AGCTCCAACTACCACAAGTT | A1 | A |
| GCACTCTTGCCTACGCCACC | A2-A | A |
| GCACTCTTGCCTACGCCACA | A2-B | A |
| GCACTCTTGCCTACGCCACG | A2-C | A |
| GCACTCTTGCCTACGCCACT | A2-D | A |
| GGTGGCGTAGGCAAGAGTGC | B1 | B |
| AACTTGTGGTAGTTGGAGCT | B2-A | B |
| AACTTGTGGTAGTTGGAGCA | B2-B | B |
| AACTTGTGGTAGTTGGAGCC | B2-C | B |
| AACTTGTGGTAGTTGGAGCG | B2-D | B |

*Underlined bases denote mutations.

During an amplification procedure involving LCR four oligonucleotides are used at a time. For example, oligonucleotide A1 and, separately, each of the A2 oligonucleotides are paired on the sense strand. Also, oligonucleotide B1 and, separately, each of the B2 oligonucleotides are paired on the antisense strand. For an LCD procedure, two oligonucleotides are paired, i.e., A1 with each of the A2 oligonucleotides, for linear amplification of the normal and mutated target DNA sequence.

The method of the invention is applicable to the detection and quantitation of other oncogenes in DNA present in various biological fluids. The p53 gene is a gene for which convenient detection and quantitation could be useful because alterations in this gene are the most common genetic anomaly in human cancer, occurring in cancers of many histologic types arising from many anatomic sites. Mutations of the p53 may occur at multiple codons within the gene but 80% are localized within 4 conserved regions, or "hot spots", in exons 5, 6, 7 and 8. The most popular current method for identifying the mutations in p53 is a multistep procedure. It involves PCR amplification of exons 5–8 from genomic DNA, individually, in combination (i.e., multiplexing), or sometimes as units of more than one exon. An alternative approach is to isolate total cellular RNA, which is transcribed with reverse transcriptase. A portion of the reaction mixture is subjected directly to PCR to amplify the regions of p53 cDNA using a pair of appropriate oligonucleotides as primers. These two types of amplification are followed by single strand conformation polymorphism analysis (SSCP) which will identify amplified samples with point mutations from normal DNA by differences in mobility when electrophoresed in polyacrylamide gel. If a fragment is shown by SSCP to contain a mutation, the latter is amplified by asymmetric PCR and the sequence determined by the dideoxy-chain termination method (Murakami et al, *Can. Res.*, 51: 3356–33612, 1991).

Further, the ligase chain reaction (LCR) may be useful with p53 since LCR is better able to evaluate multiple mutations at the same time. After determining the mutation, allele-specific primers can be prepared for subsequent quantitation of the mutated gene in the patient's plasma at multiple times during the clinical course.

Preferably, the method of the invention is conducted using biological fluid samples of approximately 5 ml. However, the method can also be practiced using smaller sample sizes in the event that specimen supply is limited. In such case, it may be advantageous to first amplify the DNA present in the sample using the common primers. Thereafter, amplification can proceed using the allele-specific primers.

The method of this invention may be embodied in diagnostic kits. Such kits may include reagents for the isolation of DNA as well as sets of primers used in the detection method, and reagents useful in the amplification. Among the reagents useful for the kit is a DNA polymerase used to effect the amplification. A preferred polymerase is *Thermus aquaticus* DNA polymerase available from Perkin-Elmer as AmpliTaq DNA polymerase. For quantitation of the mutated gene sequences, the kit can also contain samples of mutated DNA for positive controls as well as tubes for quantitation by competitive PCR having the engineered sequence in known amounts.

The quantitation of the mutated K-ras sequences may be achieved using either slot blot Southern hybridization or competitive PCR. Slot blot Southern hybridization can be a performed utilizing the allele-specific primers as probes under relatively stringent conditions as described by Verlaan-de Vries et al., *Gene* 50:313–20, 1986. The total DNA extracted from 5 ml of plasma will be slot blotted with 10 fold serial dilutions, followed by hybridization to an end-labeled allele-specific probe selected to be complementary to the known mutation in the particular patient's tumor DNA as determined previously by screening with the battery of allele-specific primers and PCR and LCR. Positive autoradiographic signals will be graded semiquantitatively by densitometery after comparison with a standard series of diluted DNA (1–500 ng) from tumor cell cultures which have the identical mutation in codon 12 of the K-ras, prepared as slot blots in the same way.

A modified competitive PCR (Gilliland et al., *Proc. Nat. Acad. Sci., USA* 87:2725:79; 1990; Gilliland et al., "Competitive PCR for Quantitation of MRNA", *PCR Protocols* (Acad. Press), pp. 60–69, 1990) could serve as a potentially more sensitive alternative to the slot blot Southern hybridization quantitation method. In this method of quantitation, the same pair or primers are utilized to amplify two DNA templates which compete with each other during the amplification process. One template is the sequence of interest in unknown amount, i.e. mutated K-ras, and the other is an engineered deletion mutant in known amount which, when amplified, yields a shorter product which can be distinguished from the amplified mutated K-ras sequence. Total DNA extracted from the plasma as described above will be quantitated utilizing slot blot Southern hybridization, utilizing a radiolabelled human repetitive sequence probe (BLURS). This will allow a quantitation of total extracted plasma DNA so that the same amount can be used in each of the PCR reactions. DNA from each patient (100 ng) will be added to a PCR master mixture containing P1 or P2 allele-specific primers corresponding to the particular mutation previously identified for each patient in a total volume of 400 µl. Forty µl of master mixture containing 10 ng of plasma DNA will be added to each of 10 tubes containing 10 µl of competitive template ranging from 0.1 to 10 attomoles. Each reaction mixture will contain dNTPs (25 µM final concentration including [$\alpha$-$^{32}$P]dCTP at 50 µCi/ml), 50 pmoles of each primer, 2 mM $MgCl_2$, 2 units of *T. aquaticus* DNA polymerase, 1×PCR buffer, 50 µg/ml BSA, and water to a final volume of 40 µl. Thirty cycles of PCR will be followed by electrophoresis of the amplified products. Bands identified by ethidium bromide will excised, counted and a ratio of K-ras sequence to deletion mutant sequence calculated. To correct for difference in molecular weight, cpm obtained for genomic K-ras bands will multiplied by 141/161 or 126/146, depending upon whether position 1 (P1) or position 2 (P2) primers are used. (The exact ratio will depend upon the length of the deletion mutant.) Data will be plotted as log ratio of deletion template DNA/K-ras DNA vs. log input deletion template DNA (Gilliland et al. 1990a, 1990b).

A modified competitive PCR could also be developed in which one primer has a modified 5' end which carries a biotin moiety and the other primer has a 5' end with a fluorescent chromophore. The amplified product can then be separated from the reaction mixture by adsorption to avidin or streptavidin attached to a solid support. The amount of product formed in the PCR can be quantitated by measuring the amount of fluorescent primer incorporated into double-stranded DNA by denaturing the immobilized DNA by alkali and thus eluting the fluorescent single stands from the solid support and measuring the fluorescence (Landgraf et al., *Anal. Biochem.* 182:231–235, 1991).

The competitive template preferably comprises engineered deletion mutants with a sequence comparable to the fragments of the wild type K-ras and the mutated K-ras gene amplified by the P1 and P2 series of primers described previously, except there will be an internal deletion of approximately 20 nucleotides. Therefore, the amplified products will be smaller, i.e., about 140 base pairs and 125 base pairs when the P1 primers and P2 primers are used, respectively. Thus, the same primers can be used and yet amplified products from the engineered mutants can be readily distinguished from the amplified genomic sequences.

Eight deletion mutants will be produced using the polymerase chain reaction (Higuchi et al., *Nucleic Acids Res.* 16:7351–67 1988); Vallette et al., *Nucleic Acids Res.* 17:723–33, 1989; Higuchi, *PCR Technology*, Ch. 6, pp. 61–70 (Stockton Press, 1989)). The starting material will be normal genomic DNA representing the wild-type K-ras or tumor DNA from tumors which are known to have each of the possible point mutations in position one and two of codon 12. The wild-type codon 12 is GGT. The following tumor DNA can be used:

First position codon 12 mutations

|       |                  |
| ----- | ---------------- |
| G→A   | A549             |
| G→T*  | Calu1, PR371     |
| G→C   | A2182, A1698     |

Second position codon 12 mutations

|       |                    |
| ----- | ------------------ |
| G→A*  | Aspc1              |
| G→T*  | SW480              |
| G→C   | 818-1, 181-4, 818-7 |

(*G→T transversions in the first or second position account for approximately 80% of the point mutations found in pulmonary carcinoma and GAT (aspartic acid) or GTT (valine) are most common in pancreatic cancer.

The deletion mutants with an approximately 20 residue deletion will be derived as previously described (Vallette et al. 1989). In summary, the P1 and P2 primers will be used in an allele-specific manner with the normal DNA or with DNA from the tumor cell line with each specific mutation. Each of these would be paired for amplification with a common primer which contains the sequence of the common primer normally used with either the P1 and P2 allele-specific primers, i.e., "P1-B" or "P2-B" at the 5' end with an attached series of residues representing sequences starting approximately 20 bases downstream, thus spanning the deleted area (common deletion primer 1 and 2, CD1 and CD2). The precise location and therefore sequence of the 3' portion of the primer will be determined after analysis of the sequence of the ras gene in this region with OLIGO (NB1, Plymouth, MN), a computer program which facilitates the selection of optimal primers. The exact length of the resultant amplified product is not critical, so the best possible primer which will produce a deletion of 20–25 residues will be selected. For example, with P2 primers the allele-specific primer for the wild-type will be 5' ACTCTTGCCTACGC-CAC 3' complementary to residues 35 to 51 in the coding sequence. To effect a deletion of approximately 20 residues in the complementary strand, the common upstream primer to be used with the wild-type and the three allele-specific primers for mutations in position two of codon 12 will be 40 residues long (CD2) complementary to residues −95 to −78 (the currently preferred common upstream primer for use with P2 allele-specific primers and residues at approximately −58 to −25). The amplified shorter product will be size-separated by gel electrophoresis and purified by Prep-a-Gene (Biorad). DNA concentrations will be determined by the ethidium bromide staining with comparison to dilutions of DNA of known concentration. This approach will be repeated eight times, using the four P1 primers and common primer (CD1) constructed as above, and four times with the four P2 primers and common primer (CD2). These deletion mutants will be amplified, using the same allele-specific primers used to amplify the genomic DNA. Therefore, they can be used subsequently in known serial dilutions in a competitive PCR, as outlined above.

The invention is further illustrated by the following non-limiting examples.

EXAMPLE 1

Blood was collected in 13×75 mm vacutainer tubes containing 0.05 ml of 15% $K_3EDTA$. The tubes were immediately centrifuged at 4° C. for 30 minutes at 1000 g, the plasma was removed and recentrifuged at 4° C. for another 30 minutes at 1000 g. The plasma was stored at −70° C. Next, DNA was deproteinized by adding an equal volume of 20% NaCl to 5 ml aliquots of plasma which were then boiled for 3 to 4 minutes. After cooling, the samples were centrifuged at 3000 rpm for 30 minutes. The supernatant was removed and dialysed against three changes of 10 mM Tris-HCl (pH 7.5)/1 mM EDTA (pH 8.0) ("TE") for 18 to 24 hours at 4° C. The DNA was extracted once with two volumes of phenol, 2×1 volume phenol:chloroform: isoamyl alcohol (25:24:1) and 2×1 volume chloroform: isoamyl alcohol (24:1). DNA was subsequently precipitated with NaCl at 0.3M, 20 µg/ml glycogen as a carrier and 2.5 volumes of 100% ethanol at minus 20° C. for 24 hours. DNA was recovered by centrifugation in an Eppendorf Centrifuge at 4° C. for 30 minutes. The DNA was then resuspended in a TE buffer. The DNA extracted and prepared in the above manner was then able to be amplified.

EXAMPLE 2

An allele-specific amplification of DNA obtained and prepared according to example 1 was conducted by PCR as follows to detect the K-ras gene in the DNA having a mutation at position 1 or 2 of the codon 12 of the K-ras gene. In each of eight reaction tubes was added DNA extracted from 0.5 ml of plasma in total volume of 40 µl containing 67 mM Tris-HCl (pH 8.8), 10 mM β-mercaptoethanol, 16.6 µM ammonium sulfate, 6.7 µM EDTA, 2.0 mM, $MgCl_2$, 50 µg/ml BSA, 25 µM dNTP. Also, 50 pmoles of each of the primers identified in Table 1 was included, together with 3 units of *Thermus aquaticus* DNA polymerase (available from Perkin-Elmer as AmpliTaq). PCR was conducted with an initial denaturation at 95° C. for 5 minutes, followed by 30 cycles of PCR amplification in a DNA thermal cycler (Cetus; Perkin-Elmer Corp. Norwalk, Conn.). Each amplification cycle includes a 1 minute denaturation at 95° C., a 2 minute primer annealing period at 58° C., and a 1 minute extension period at 72° C.

Following the completion of amplification, 10–15 µl of each of the PCR reaction products is analyzed by electrophoresis in a 2% agarose gel/1× TAE-0.5 µg/ml EtBr. The electrophoresis uses an applied voltage of 100 volts for 90 minutes. Photographs of the samples are then taken using ultraviolet light under standard conditions.

It is understood that various modifications can be made to the present invention without departing from the scope of the claimed invention.

I claim:

1. A method of detecting a mutant allele, comprising the steps of:

providing a sample of a biological fluid containing soluble DNA, including a mutant allele of interest;

deproteinizing the DNA and substantially simultaneously therewith inactivating any DNases present in the sample;

extracting the DNA from the sample;

denaturing the DNA to dissociate first and second strands of the DNA;

amplifying the mutant allele of interest in an allele-specific manner using at least a first set of four allele-specific oligodeoxynucleotide primers having one primer the 3' terminal nucleotide of which is complementary to a mutation-containing segment on a first strand of the DNA and a first common oligodeoxy-nucleotide primer for pairing during amplification to each allele-specific oligodeoxynucleotide primer, the common oligodeoxynucleotide primer being complementary to a segment of a second strand of the DNA distant with respect to the position of the first oligodeoxynucleotide primer; and detecting the presence of the mutant allele of interest.

2. The method of claim 1, wherein the mutant allele is amplified in an allele-specific manner using the polymerase chain reaction (PCR).

3. The method of claim 2, wherein following the amplification step, the step of detecting the presence of the mutant allele of interest comprises performing an allele-specific ligase chain reaction (LCR) or a ligase detection reaction (LDR) using the amplified product of PCR.

4. The method of claim 1 wherein protein is removed and DNases are inactivated by adding a salt solution to the sample and subsequently boiling the sample.

5. The method of claim 1, wherein the biological fluid is selected from the group consisting of whole blood, serum, plasma, urine, sputum, and cerebral spinal fluid.

6. The method of claim 1 wherein the mutant allele comprises a gene sequence having a point mutation at a known location.

7. The method of claim 6 wherein the first DNA strand is the sense strand and the second DNA strand is the antisense strand.

8. The method of claim 1 wherein the step of amplifying the mutant allele with the PCR is conducted using a DNA polymerase which lacks the 3' exonuclease activity and therefore the ability to repair single nucleotide mismatches at the 3' end of the primer.

9. The method of claim 8 wherein the DNA polymerase is a *Thermus aquaticus* DNA polymerase.

10. The method of claim 8 wherein the first set of allele-specific oligodeoxynucleotide primers comprises:

four oligodeoxynucleotide sense primers, one of which has a 3' terminal nucleotide complementary to a point mutation of the sense strand, another of which has a 3' terminal nucleotide complementary to the wild type nucleotide for the segment to be amplified, and the remaining two of which have 3' terminal nucleotides complementary to the remaining two possible mutations at the mutated point of the sense strand; and a common oligodeoxynucleotide antisense primer complementary to a segment of the antisense strand distant from the location on the sense strand at which the oligodeoxynucleotide sense primers will anneal, the common oligodeoxynucleotide antisense primer being paired with each of the oligodeoxynucleotide sense primers during amplification.

11. The method of claim 10 wherein the 3' terminal nucleotide of the complementary oligodeoxynucleotide sense primer anneals with the mutated nucleotide of the sense strand.

12. The method of claim 2 wherein the mutant allele comprises a gene sequence having a point mutation at one of two known locations.

13. The method of claim 12 wherein the step of amplifying the mutant allele through the PCR further comprises the use of a second set of four allele-specific oligodeoxynucleotide primers, in conjunction with the first set, wherein the second set of allele-specific oligodeoxynucleotide primers comprises:

four oligodeoxynucleotide sense primers, one of which has a 3' terminal nucleotide complementary to a point mutation of the sense strand, another of which has a 3' nucleotide complementary to the wild type nucleotide of the segment to be amplified, and the remaining two of which have 3' terminal nucleotides complementary to the remaining two possible mutations at the mutated point of the sense strand; and a common oligodeoxynucleotide antisense primer complementary to a segment of the antisense strand distant from the location on the sense strand at which the oligodeoxynucleotide sense primers will anneal, the common oligodeoxynucleotide antisense primer being paired with each of the oligodeoxynucleotide sense primers during amplification.

14. The method of claim 13 wherein the 3' terminal nucleotide of the complementary oligodeoxynucleotide sense primer anneals with the mutated nucleotide of the sense strand.

15. The method of claim 14 wherein the mutant allele to be detected is the K-ras gene sequence having a mutation at position 1 or 2 in the twelfth codon.

16. The method of claim 15 wherein the first set of allele-specific oligodeoxynucleotide primers comprises oligodeoxynucleotide sense primers consisting of the following sequences

SEQ ID NO: 1
SEQ ID NO: 2
SEQ ID NO: 3
SEQ ID NO: 4 and the common oligodeoxynucleotide antisense primer consisting of the following sequence

SEQ ID NO: 5.

17. The method of claim 13 wherein the second set of allele-specific oligodeoxynucleotide primers comprises oligodeoxynucleotide sense primers consisting of the following sequences

SEQ ID NO: 6
SEQ ID NO: 7
SEQ ID NO: 9
SEQ ID NO: 8 and the common oligodeoxynucleotide antisense primer consisting of the following sequence

SEQ ID NO: 10.

18. The method of claim 1 wherein the step of detecting the presence of amplified DNA is conducted by gel electrophoresis in 1–5% agarose gel.

19. The method of claim 18 wherein the biological fluid is selected from the group consisting of whole blood, serum, plasma, urine, sputum, and cerebral spinal fluid.

20. A diagnostic kit for detecting the presence of a K-ras mutation in the nucleic acids in biological fluid, wherein the mutation is present in the twelfth codon at position 1, comprising:

reagents to facilitate the deproteinization and isolation of DNA;

reagents to facilitate amplification by the polymerase chain reaction;

a heat stable DNA polymerase; and a first set of allele-specific oligodeoxynucleotide sense primers having the following sequences
SEQ ID NO: 1
SEQ ID NO: 2
SEQ ID NO: 3
SEQ ID NO 4 and a first common oligodeoxynucleotide antisense primer having the following sequence
SEQ ID NO: 5.

21. The diagnostic kit of claim 20 further comprising a second set of allele-specific oligodeoxynucleotide sense primers having the following sequences
SEQ ID NO: 6
SEQ ID NO: 7
SEQ ID NO: 9
SEQ ID NO: 8 and a second common oligodeoxynucleotide antisense primer having the following sequence
SEQ ID NO: 10.

wherein the second set of allele-specific oligodeoxynucleotide primers and the second common oligodeoxynucleotide primer are useful in detecting in biological fluid the presence of a mutated K-ras gene sequence in the twelfth codon at position 2.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:1:

GTGGTAGTTG    GAGCTG        16

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:2:

GTGGTAGTTG    GAGCTC        16

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:3:

GTGGTAGTTG    GAGCTT        16

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:4:

GTGGTAGTTG    GAGCTA        16

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:5:

CAGAGAAACC    TTTATCTG        18

( 2 ) INFORMATION FOR SEQ ID NO:6:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (i i) MOLECULE TYPE: DNA (i i i) SEQUENCE DESCRIPTION: SEQ ID NO:6:

ACTCTTGCCT ACGCCAC 17

(2) INFORMATION FOR SEQ ID NO:7:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (i i i) SEQUENCE DESCRIPTION: SEQ ID NO:7:

ACTCTTGCCT ACGCCAG 17

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (i i i) SEQUENCE DESCRIPTION: SEQ ID NO:8:

ACTCTTGCCT ACGCCAA 17

(2) INFORMATION FOR SEQ ID NO:9:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (i i i) SEQUENCE DESCRIPTION: SEQ ID NO:9:

ACTCTTGCCT ACGCCAT 17

(2) INFORMATION FOR SEQ ID NO:10:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (i i i) SEQUENCE DESCRIPTION: SEQ ID NO:10:

GTACTGGTGG AGTATTT 17

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA ( i i i ) SEQUENCE DESCRIPTION: SEQ ID NO:11:

AGCTCCAACT ACCACAAGTT       20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:12:

GCACTCTTGC CTACGCCACC       20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:13:

GCACTCTTGC CTACGCCACA       20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:14:

GCACTCTTGC CTACGCCACG       20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:15:

GCACTCTTGC CTACGCCACT       20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:16:

GGTGGCGTAG GCAAGAGTGC       20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:17:

```
AACTTGTGGT    AGTTGGAGCT                    20
```

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:18:

```
AACTTGTGGT    AGTTGGAGCA                    20
```

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:19:

```
AACTTGTGGT    AGTTGGAGCC                    20
```

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) SEQUENCE DESCRIPTION: SEQ ID NO:20:

```
AACTTGTGGT    AGTTGGAGCG                    20
```